United States Patent [19]

Dugle et al.

[11] 4,076,502
[45] Feb. 28, 1978

[54] METHOD, COMPOSITION, AND DEVICE FOR DETERMINING THE SPECIFIC GRAVITY OF A LIQUID

[75] Inventors: James B. Dugle; C. Bradley Hager, both of Elkhart, Ind.

[73] Assignee: Miles Laboratories, Inc., Elkhart, Ind.

[21] Appl. No.: 696,050

[22] Filed: Jun. 14, 1976

Related U.S. Application Data

[63] Continuation of Ser. No. 549,944, Feb. 14, 1975, abandoned.

[51] Int. Cl.² ............... G01N 31/14; G01N 31/22; G01N 33/16
[52] U.S. Cl. .................. 23/230 R; 23/253 TP; 195/103.5 C; 252/408
[58] Field of Search .............. 23/253 TP, 230 R; 195/103.5 C; 252/408

[56] References Cited

U.S. PATENT DOCUMENTS

| 2,785,958 | 3/1957 | Copenhefer et al. | 23/253 TP |
|---|---|---|---|
| 2,848,308 | 8/1958 | Free | 23/253 TP |
| 2,999,793 | 9/1961 | Babson | 195/103.5 |
| 3,011,874 | 12/1961 | Deutsch | 23/253 TP |
| 3,050,373 | 8/1962 | Collins | 23/253 TP |
| 3,278,394 | 10/1966 | Harvill et al. | 195/103.5 |
| 3,349,006 | 10/1967 | Albaum | 195/103.5 |
| 3,395,082 | 7/1968 | Mast | 195/103.5 |
| 3,410,757 | 11/1968 | Fraser | 195/103.5 |
| 3,443,903 | 5/1969 | Maack et al. | 23/253 TP |
| 3,507,269 | 4/1970 | Berry | 23/253 TP |
| 3,598,704 | 8/1971 | Dahlqvist | 195/103.5 |
| 3,663,374 | 5/1972 | Moyer et al. | 195/103.5 |

Primary Examiner—Robert M. Reese
Attorney, Agent, or Firm—Andrew L. Klawitter

[57] ABSTRACT

A method, composition, and device for determining the specific gravity of a liquid. In the method, a sample of the liquid to be tested is contacted with standardized quantities of substances which participate in a reaction that is affected by the level of solute in said liquid. The resulting effect of the solute on the reaction is a reproducible function of the concentration or amount of solute in the sample and relates to the specific gravity of the liquid tested. A unitized test composition is provided comprising at least one substance which participates in the standardized reaction. The standardized reaction is preferably chemical in nature and, in such a case, the test composition preferably includes an indicator responsive to a product of the chemical reaction.

31 Claims, 7 Drawing Figures

METHOD, COMPOSITION, AND DEVICE FOR DETERMINING THE SPECIFIC GRAVITY OF A LIQUID

This is a continuation, of application Ser. No. 549,944, filed Feb. 14, 1975, now abandoned.

BACKGROUND OF THE INVENTION

1. Field of the Invention

This invention relates to methods, compositions, and devices for determining the specific gravity of a liquid. In particular, this invention relates to means for determining the specific gravity of an aqueous liquid. The present invention finds application in the determination of the specific gravity of body fluids such as urine.

Specific gravity is defined as the ratio of the density of a substance to that of a standard substance. Where the substance whose specific gravity is to be determined is in a liquid form, the standard substance generally is water. In the context of this disclosure, a liquid whose specific gravity is to be determined shall be defined as a mixture of substances whose aggregate is in a homogenous liquid state. The substance in the liquid that is present in the greatest amount shall be defined as the solvent or solvent component with the remaining substance or substances being defined as the solute.

Specific gravity determinations are used in the fields of science, medicine, and industry for a wide variety of purposes. For example, it is often quite useful to ascertain the specific gravity of an unknown liquid to aid in identification thereof. The determination of the specific gravity of body fluids, particularly urine, is a part of nearly all routine urinalyses. Urine consists of water as solvent and various dissolved solids as solute. Only a minor portion, if any, of the solute component of urine consists of liquid substances. Thus, the specific gravity of urine indicates the relative proportions of dissolved solid components to the total volume of the specimen tested and therefore reflects the relative degree of concentration or dilution of the specimen. Under appropriate and standardized conditions of fluid restriction or increased uptake, the specific gravity of a urine specimen measures the concentrating and diluting abilities of the kidney.

Normal urinary specific gravity ranges from 1.003 to 1.035, but usually remains between 1.010 and 1.025. Specific gravities below 1.010 can be indicative of diabetes insipidus, a disease caused by the absence of, or impairment to, the normal functioning of the antidiuretic hormone. Low specific gravity may also occur in patients with glomerulonephritis, pyelonephritis, and various renal anomalies. Specific gravity is high in patients with diabetes mellitus, adrenal insufficiency, hepatic disease, and congestive cardiac failure. Therefore, urinary specific gravity determinations are useful in routine urinalysis as a screening procedure for detecting potentially abnormal clinical conditions.

2. Description of the Prior Art

By its definition, the most straight forward method for determining the specific gravity of a liquid is to determine the ratio of the weight of a given volume of the liquid to the weight of the same volume of water under standard conditions. Such a method, however, requires precise volumetric and gravimetric techniques. More often, the specific gravity of liquids is determined using pycnometers or gravitometers. Such instruments have as their principle the fact that, if two manometers containing liquids of different densities are connected to a common source of suction, the heights of the liquids are inversely proportional to their densities, and hence their specific gravities.

In the clinical laboratory, urinary specific gravity is determined in many ways. The specific gravity of urine is usually determined with a urinometer. A urinometer is a weighted bulb-shaped device having a cylindrical stem which contains a scale calibrated in units of specific gravity. The device is floated in a cylinder containing the urine. The depth to which the device sinks in the urine indicates the specific gravity of the urine and is read on the scale at the surface of the urine. The urinometer is sensitive to temperature requiring an adjustment of 0.001 units for each 3° C. difference between the calibrated temperature of the device and the temperature of the urine specimen.

All of the methods and devices mentioned hereinabove for determining the specific gravity of a liquid require a relatively large sample volume in order to conduct the test. The need for a several milliliter volume of sample sometimes requires that an additional urine specimen must be obtained from the patient, thereby destroying the continuity of routine urinalysis. It is most desirable to obtain all of the routine urinalysis results from a single sample in order that the relationships between the test results may be properly analyzed.

Through the use of a refractometer, urinary specific gravity determinations may be carried out using as little as one drop of urine. Since in urine the solute consists essentially of only dissolved solids, the refractive index of urine closely correlates with its specific gravity. Small hand refractometers are available specifically designed for determining urinary specific gravity.

Many other diverse techniques are available for determining the specific gravity of a liquid. All of the known techniques require a bulky instrument or device of one sort or another which has to be consistently cleaned, maintained, and adjusted in order to produce reliable results. All such techniques also are based strictly on physical measurements such as measurements of volume, weight, height, and refractive index.

Routine urinalysis, as practiced at the present time, involves three basic areas of investigation: a determination of the presence or absence of substances such as glucose, protein, occult blood, ketones, and so forth; a determination of specific gravity; and a microscopic examination of the urinary sediment. The first area of investigation usually involves the testing of the urine specimen with indicator papers or strips comprising reagent pads responsive to the urinary constituents to be determined. Indicator strips, usually in the form of single strips carrying multiple reagent pads responsive to the different urinary constituents to be determined, are dipped momentarily into the urine specimens, and the resulting color responses are compared to a color chart. Under present technology, separate analytical steps must be undertaken to determine urinary specific gravity and to microscopically examine the urinary sediment.

SUMMARY OF THE INVENTION

A new means for determining the specific gravity of a liquid has now been discovered. By the new means of the present invention specific gravity can be determined without requiring elaborate physical measurements or instrumental hardware. A method, test composition and device are provided which yield a response, preferably a colorimetric response, related to the specific gravity of a liquid contacted with the composition or device. One form of the device of the present invention is that of a reagent pad of the type used in the prior art for determining urinary constituents. Thus, such a reagent pad for determining urinary specific gravity may be readily included on an indicator strip which carries multiple reagent pads responsive to the different urinary constituents of interest. A multiple reagent strip therefore can be made which provides a means for determining urinary constituents and specific gravity simultaneously, thereby eliminating the additional analytical steps required in the prior art for determining urinary specific gravity.

The present invention is based on the observation that specific standardized reactions which occur in the liquid whose specific gravity is to be determined, are affected by the level of solute present. Specifically, the present method comprises contacting the liquid to be tested with at least one substance capable of producing, on said contact, a predetermined reaction when the liquid contains a known amount of solute, and also capable of producing, on said contact, an aberration of the reaction when the liquid contains a different amount of solute. The specific gravity of the liquid may then be determined by the extent of any resulting aberration of the reaction.

DESCRIPTION OF THE PREFERRED EMBODIMENTS

The types of reactions contemplated by the present invention include those which involve a chemical or physical interaction which occurs, usually on a molecular level, in a liquid medium of the type whose specific gravity is to be determined and which is affected by the amount or concentration of solute in the liquid medium. Chemical reactions are preferred, since means for evaluating aberrations of chemical reactions are readily available. Usually, the liquid to be tested is contacted with the components of the standardized reaction and is additionally contacted with an indicator responsive to any aberration in the reaction which may occur due to the level of solute in the liquid.

The indicator may be responsive to either physical or chemical aberrations and hence may function in a spectrophotometric, potentiometric, manometric, thermal, radiological, or turbidometric manner. Preferably the indicator consists primarily of one or more chemical reagents which produce a colorimetric response either to the presence or absence of the aberration in the standardized test reaction. In this way, the effect on the standardized test reaction of the presence of solute in the liquid to be tested may be determined either by a visual or instrumental observation of the indicator response.

Normally, the results observed in a test run are compared to those observed in standard runs, and an aberration from standard results provides a measure of the specific gravity of the test liquid. The results of the standard runs are usually in the form of a standard graph plot or, where the preferred colorimetric indicators are used, a standard color chart. The comparison that is made between the aberration, if any, produced in the test run and the standard results can be accomplished automatically by instrument means, for example, where a single instrument observes the aberration and internally compares it to the standard, thereby yielding an output in units of specific gravity. Due to its convenient nature, the present invention is particularly suited to an uncomplicated test strip format. In one aspect, the present invention provides a "dip-and-read" type test device which yields a colorimetric response related to specific gravity within a less than two minute period of time after momentary immersion in the liquid to be tested.

Of the chemical reactions which are preferably utilized according to the present invention, those whose rate is affected, either enhanced or inhibited by the solute, are particularly useful. Usually the rate of the chemical reaction is inhibited as the level of solute increases. Also, the chemical reaction preferably is one that produces a product. Any aberration in the reaction is readily determinable by monitoring the rate of disappearance of a reactant or the rate of appearance of a product. The rate of appearance of a product is usually more readily determinable particularly where an indicator for the product is present during the reaction. By choosing an indicator which yields a colorimetric response to the presence or absence of a product of the reaction, any effect that the presence of the test liquid has on the reaction results in an effect on the color change. When the aberration of the reaction due to the presence of solute in the test liquid is an effect on the rate of the reaction, test liquids having different specific gravities will produce different rates of color change. Thus, in such a case, the actual color change that occurs after a predetermined period of time is related to the specific gravity of the liquid tested.

Numerous chemical reactions have been found to be affected by the level of solute in a liquid medium in which they occur. Various chemical reactions of this type are pointed out in the examples which follow. Particularly preferred are those chemical reactions which may be catalyzed by an enzyme. The specific activity of enzymes has been found to be especially sensitive to the level of environmental solute, particularly dissolved solids. Exemplary of enzymatic reactions which may be used in accordance with the present invention are those which involve the action of enzymes which are classified as transferases, hydrolases, lyases, isomerases, and ligases. Particularly useful are those reactions catalyzed by the oxidoreductases, especially those which catalyze the oxidation of a carbohydrate such as a hexose.

Of the reactions which are catalyzed by an oxidoreductase, those involving the action of an oxidase have been found to yield particularly reproducible and distinct aberrations related to specific gravity. Oxidase reactions which yield a peroxide, particularly hydrogen peroxide, as a product are preferred, since indicators responsive to peroxide are well known in the art. Exemplary of oxidase reactions are those which involve the enzymatic oxidation of glycollate, malate, cholesterol, aryl alcohol, gulonolactone, pyranose, pyridoxin, alcohol, catechol, hydroxyacids, hypoxanthine, xanthine, glycine, L-amino acid, D-amino acid, uric acid, luciferin, aspartic acid, lactic acid, and various mono- and di-amines, and aliphatic and aromatic aldehydes. Particularly preferred are the hexose oxidase reactions such as those involving the oxidation of glucose, galactose, or sorbose.

Indicators which are particularly suited to detecting the presence of peroxides, such as hydrogen peroxide, in liquids comprise a substance having peroxidative activity and a chromogen which is oxidized in the presence of peroxide and the substance having peroxidative activity to yield a spectrophotometric response, usually in the visible range. Such chromogens include those which are oxidation-reduction types having a potential appropriate to detecting the particular peroxide in the presence of the substance having peroxidative activity. Such chromogens thus include, water soluble iodide salts, o-tolidine, syringaldazine, vanillinazine, the combination of phenol and 4-aminoantipyrine, 2,7-diaminofluorene, benzidine and derivatives thereof such as o-dianisidine. Substances having peroxidative activity comprise such naturally occurring peroxidases as horseradish peroxidase and potato peroxidase. Other substances having peroxidative activity include materials such as normal whole blood, red blood cells alone, lyophilized whole blood, urohemin, metalloporphyrins, and so forth. Certain inorganic compounds, such as the combination of iodide and molybdate salts, may also be used as an indicator.

The basic first step of the method of the present invention comprises contacting the liquid to be tested with the substance or substances necessary for the reaction that is affected by the level of solute in said liquid. Thus, in one aspect, such first step involves the combination or intermixing of the test liquid with the necessary reaction constituents. It is important to standardize the reaction within certain parameter ranges in order to be sufficiently confident that any significant aberration of the reaction due to the presence of solute in the test liquid is a function essentially only of the level of solute present. It is usually sufficient to standardize the amounts or concentrations of the reaction constituents, i.e. reactants, catalysts, and so forth, and the environmental reaction conditions, such as temperature and pressure. The critical allowable ranges for such reaction parameters will of course vary from one type of reaction to another. The essence of the present invention in this regard is strictly empirical.

Standardization of the environmental reaction conditions is usually a relatively simple matter, since, for the sake of convenience, the reaction is normally conducted under room conditions. The slight variations in temperature and pressure that may occur under room conditions usually have little, if any, effect on reactions selected for use in the present invention. The degree of control of the amounts or concentrations of the reaction constituents required for standardization purposes depends upon the sensitivity of the specific gravity-induced aberration produced in a particular reaction. For instance, where varying the amount of a particular reaction constituent does not significantly affect the specific gravity-induced aberration, precise control of the amount of such constituent used would not be required. Such a situation may exist where the chosen reaction is one whose rate is affected by specific gravity and which involves the action of a catalyst which may be present in widely varying amounts or concentrations without affecting the reaction rate. In such a situation, control of the quantity of catalyst present would not be critical. In other circumstances, the amount of catalyst present may affect reaction rate and would, therefore, be subject to critical limitations.

Some of the reactions which are sensitive to specific gravity in the manner of the present invention involve reaction constituents which are normally present in relatively constant amounts or concentrations in the atmosphere or in the liquid to be tested. One substance which is present in the liquid to be tested at a relatively fixed concentration is the solvent portion thereof. It is contemplated that a particular reaction selected for use in the present invention could include the solvent as a reaction constituent. If the level of solvent is critical to the standardization of the reaction, the volume of sample tested should be predetermined, thereby standardizing the level of solvent present.

Substances which are present in the atmosphere in relatively constant amounts and which may participate in a reaction selected in accordance with the present invention are the atmospheric gases, particularly oxygen. Many of the reactions which are contemplated by the present invention require atmospheric oxygen as a reaction constituent. This is particularly true of the most preferred reactions, namely, those involving the enzymatic oxidation of a carbohydrate. Where a reaction of this type is involved, such an atmospheric reaction constituent is automatically standardized by carrying out the reaction under ordinary room conditions.

Therefore, the first basic step of the present method generally comprises contacting the liquid to be tested with standardized quantities of all of the substances which participate in the chosen specific gravity-affected reaction. Where one or more of the reaction constituents is present in the atmosphere, i.e., atmospheric reaction constituents, such a step may be accomplished by contacting the liquid to be tested with predetermined quantities of all of the non-atmospheric reaction constituents under standardized atmospheric conditions.

The test composition provided by the present invention thus comprises at least one substance, and usually at least two substances, capable of producing, upon contacting the liquid to be tested, a predetermined reaction when the liquid contains a known amount of solute, and also capable of producing, upon said contact, an aberration of said reaction when the liquid contains a different amount of solute. Additionally, the test composition preferably comprises indicator means responsive to the aberration as described previously herein. Where the chosen reaction is catalyzed by an enzyme, the test composition preferably includes the enzyme. Where one or more of the reaction constituents is provided in a standardized quantity by the atmosphere, the test composition preferably comprises only the non-atmospheric reaction constituents.

It should be noted that it is necessary to maintain the various reaction constituents in a non-reactive relationship at least until the time of contact thereof with the liquid to be tested. Usually the test composition is so constituted that the reaction constituents are brought into reactive relationship upon contact with the liquid to be tested. Normally the chosen reaction is one which occurs in a liquid of the type to be tested but which does not occur to any significant degree in a dry state or in certain other liquids. Thus, the test composition, prior to use, may be in a dry form, such as a powder, or may be in the form of a solution or suspension in which the reaction does not occur to a significant degree. The reaction constituents comprising the test composition may also be kept separated, to be combined at the time of use.

To provide a useful test device according to the present invention, the test composition is usually incorporated with one or more carrier members. Suitable carrier members are usually constructed of material which is relatively inert with respect to the reaction constituents, porous and/or absorbent relative to the liquid to be tested. Such carrier members include bibulous paper; polymeric matrixes in the form of films, membranes, fleeces or the like, and so forth. The test composition or any portion thereof may be incorporated with a particular carrier member by impregnating the carrier member with a solution or dispersion of the composition, followed by drying; by coating the composition on the carrier member; by physically entrapping the composition within the carrier member; by chemically or physically bonding the composition to the carrier member; and so forth. A carrier member incorporated with the test composition or a portion thereof may be attached or otherwise associated with a base member or support as will be described more fully hereinafter. Useful base members or supports are usually in a strip form and may be constructed of plastic, paper, wood, metal foil, or the like.

Figure 1:
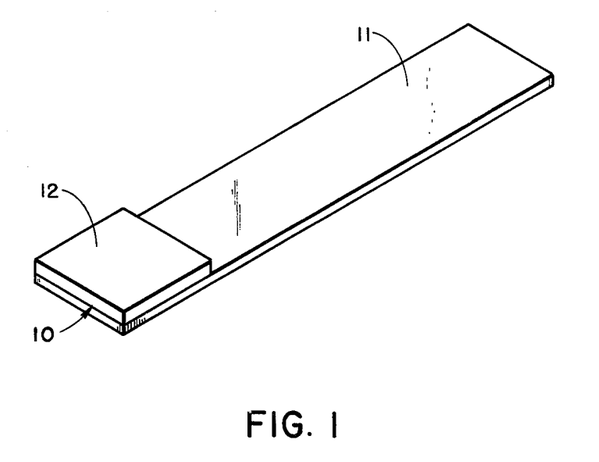
FIGS. 1, 2, 3, and 4 are perspective views of preferred forms of the test device of the present invention.

With reference to the drawing, FIG. 1 shows a test device 10 comprising an elongated rectangular strip forming a base member 11 to which member is attached a liquid absorbent carrier member 12. In one form of test device 10, the base member is formed of transparent organoplastic material and the carrier member 12 is formed of bibulous paper incorporated with at least one, but less than all, of the non-atmospheric substances which participate in a reaction selected for use in the present invention. In use, the remaining non-atmospheric substances which participate in the selected reaction and not incorporated with carrier member 12 are added to a sample of the liquid to be tested, and the carrier member 12 is momentarily dipped into or otherwise contacted with the resulting mixture, allowing the selected reaction to take place. Any resulting aberration of the reaction is detected by indicator means incorporated with carrier member 12 or added to the liquid test sample either before or after contact of carrier member 12 therewith. Depending upon whether the indicator means is incorporated with carrier member 12 or is added to the test sample, the indicator response may be observed either on carrier member 12 or in the liquid test sample after removal of carrier member 12 therefrom. Preferably, colorimetric indicator means are incorporated with carrier member 12 so that the resulting colorimetric response may be observed on or in carrier member 12 after removal from the test sample.

In a second and preferred form of test device 10, all of the non-atmospheric reaction constituents, together with indicator means; are incorporated in carrier member 12. In use of this second form of test device 10, carrier member 12 is momentarily dipped into or otherwise contacted with a sample of the liquid to be tested, thereby initiating the reaction. Upon removal of carrier member 12 from the test sample and after any incubation or response-development period which may be required, any resulting aberration is detectable on carrier member 12. When a colorimetric indicator is used as the indicator means, the preferred form of test device 10 provides a convenient "dip-and-read" type test device for determining the specific gravity of a test liquid. Certain precautions must be taken in order to insure that the reaction constituents incorporated with carrier member 12 do not react with each other to any significant degree before contact with the test liquid. This may be accomplished by various methods. One method is to impregnate carrier member 12 with a solution or suspension of the reaction constituents which consists of a solvent or liquid in which the selected reaction will not occur. A second method is to impregnate carrier member 12 with a solution or suspension of the reaction constituents, at least one of which is dispersed or encapulated in a polymeric material which is soluble in the test liquid but which is insoluble in the solution used to impregnate carrier member 12. A third method is to impregnate carrier member 12 with a first solution containing at least one, but less than all, of the reaction constituents, drying carrier member 12, and then impregnating carrier member 12 with at least one additional solution which contains the remainder of the reaction constituents and in which the reaction is incapable of occurring to a significant degree. In each of the three cases described, carrier member 12 is subjected to a final drying step and attached to base member 11.

Figure 2:
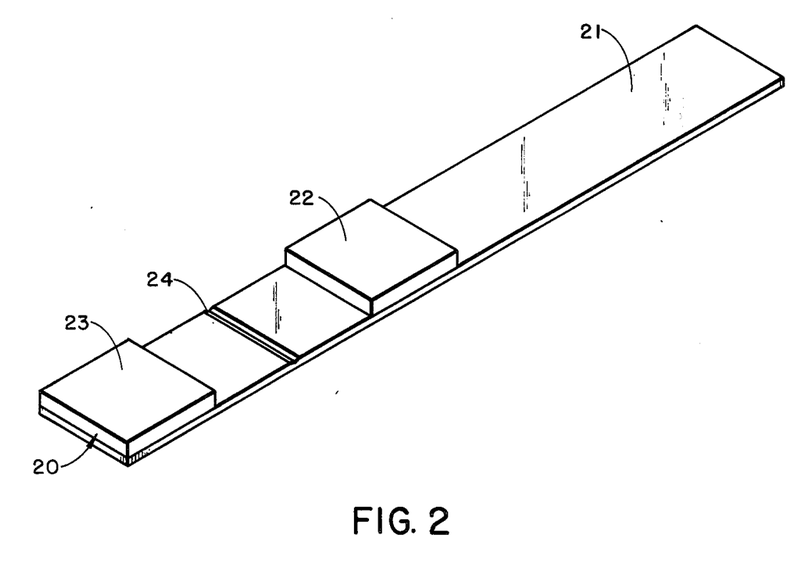

Another form of a test device of the present invention is shown in FIG. 2. A test device 20 comprises an elongated strip base member 21 to which are attached carrier members 22 and 23 which are similar to carrier member 12 in device 10. Base member 21 is formed with a transversely extending area of reduced cross-section 24 providing an integral flexible hinge allowing the portion of base member 21 bearing carrier member 23 to be bent or folded at the hinge portion 24 and relative to the remaining portion of base member 21 such that the major exposed, i.e. upper, surfaces of carrier members 22 and 23 may be brought into contact. In one form of test device 20, one of the carrier members 22 and 23 is incorporated with at least one, but not all, of the reaction constituents, the remainder of the reaction constituents being incorporated with the other of said carrier member. Either or both of carrier members 22 and 23 may also be incorporated with appropriate indicator means. In use, one or both of carrier members 22 and 23 are momentarily dipped into or otherwise contacted with the test liquid and thereafter are brought into contact with one another as previously described by folding at the hinge portion 24 to allow the selected reaction to occur on such contact. In another form of the test device 20, carrier member 23 is incorporated with some or all of the reaction constituents in a manner described previously relative to test device 10, and a colorimetric indicator composition is incorporated with carrier member 22. Any test constituents not incorporated with carrier member 23 are either added to the test sample or incorporated with the carrier member 22. In use, carrier member 23 is momentarily dipped into or otherwise contacted with the test liquid, and thereafter carrier members 22 and 23 are brought into contact with one another by folding at the hinge portion 24 to provide an indicator response on either carrier member 22 or on both of carrier members 22 and 23.

Figure 3:
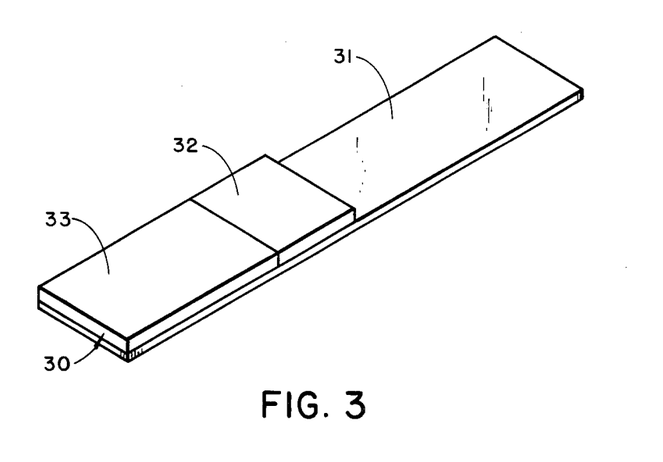

FIG. 3 shows test device 30 comprising an elongated strip base member 31 and two distinct carrier members 32 and 33 attached thereto and in edgewise abutting contact with one another. In one form of test device 30, one of the carrier members 31 and 32 is incorporated with some, but not all, of the reaction constituents, the remainder being incorporated with the other of said carrier members. In use, the end portion of carrier member 33 which is remote from carrier member 32 is dipped into or otherwise contacted with the test liquid. Carrier member 33 is formed of material of sufficient absorbency or capillarity to promote the movement of the test fluid longitudinally through carrier member 33 and into carrier member 32. The test fluid carries the reaction constituents from carrier member 33 into carrier member 32 for reaction with the constituents in carrier member 32. Either or both of carrier members 32 and 33 may also be incorporated with an appropriate indicator means. In another form of test device 30, carrier member 32 is incorporated with all of the reaction constituents, and preferably also with an indicator composition in the manner described with respect to the test device 10. Carrier member 33 may be incorporated with an indicator composition and may comprise materials for removing interfering substances from the test liquid, either by chemical or physical means, as it flows through carrier member 33 toward carrier member 32. Some interfering materials, as will be discussed more fully below, may be eliminated or rendered harmless by mere exposure to the atmosphere as the test fluid flows through carrier member 33, in which case carrier member 33 may comprise only absorbent material.

Figure 4:
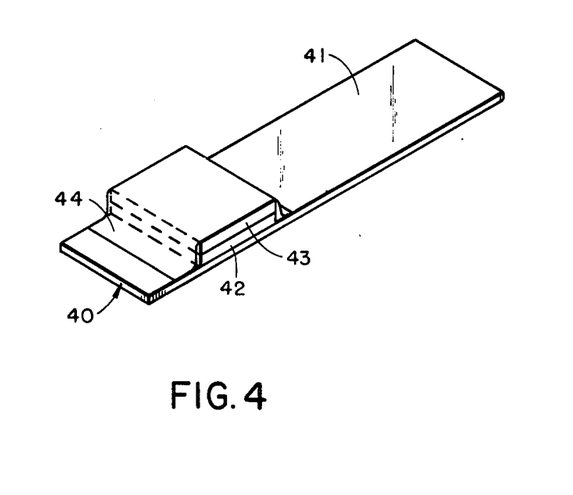

A test device 40 is shown in FIG. 4 which comprises an elongated transparent strip base member 41 and carrier members 42 and 43 attached thereto in laminate relation by means of a thin transparent plastic sheet 44 overlaying said carrier members and attached to base member 41 at opposite ends of the laminate structure comprised of carrier members 42 and 43. Carrier members 42 and 43 are incorporated with the reaction constituents, and preferably an indicator means, in the same manner as carrier members 22 and 23 in test device 20. In use, carrier members 42 and 43 are momentarily dipped into or otherwise contacted with the test liquid, and the indicator response is observed on carrier member 43 through the sheet 44 or on carrier member 42 through base member 41.

The present invention is particularly suited for the determination of specific gravity of liquids which have solutes consisting essentially of dissolved solids only. It has been found that for the purposes of the present invention the total dissolved solids content of a test liquid reproducibly affects a selected reaction of the present invention substantially independent of the proportion of the individual substances making up the total level of said dissolved solids. The test liquid is generally aqueous and usually comprises water as its solvent component. Thus, the present invention is particularly useful in determining urinary specific gravity.

In testing the specific gravity of urine with test compositions and devices of the present invention, certain interfering reactions may affect the preferred colorimetric indicator compositions. Such reactions are usually due to abnormally high levels of substances which cause certain indicator compositions to yield an erroneous response. Such interfering reactions may be eliminated either by using an indicator composition which is not significantly affected by the presence of substances which cause erroneous results with other indicator compositions, or by pre-treating the urine sample so as to remove or render harmless such interfering substance. Such pre-treatment may be accomplished by adding appropriate reagents to the urine sample before contact with the test composition or by the use of a test device as shown in FIG. 3 incorporated with such appropriate reagents. Some of the preferred colorimetric indicator materials responsive to peroxide may be interfered with where the urine sample contains ascorbic acid levels exceeding about 5 mg./100 ml. Such ascorbate interference may be avoided by using an alternate indicator material that is not affected substantially by the presence of ascorbic acid, for example, a tribromo-phenol-aminoantipyrine indicator as disclosed in Clin. Chem. 19:522(1973). Alternatively, the urine sample may be pre-treated with a weak oxidizing agent in order to eliminate ascorbic acid interference. A test device as in FIG. 3 may be so constructed that prior to reaction, the urine sample must pass through the carrier member 33 which is fabricated so as to prevent ascorbic acid from reaching the test composition in carrier member 32. This may be accomplished by forming carrier member 33 of a material which retards the capillary flow of ascorbic acid therethrough. For this purpose ion exchange papers may be utilized. Also, the carrier member 33 may be constructed of highly fibrous material such as filter paper to allow aerobic oxidation of ascorbic acid to occur as it travels through said carrier member. Materials which chemically alter ascorbic acid may also be incorporated in the carrier member 33. For example, the carrier member 33 may contain a weak oxidizing agent or an ascorbic acid metabolizing system, such as an ascorbic acid oxidase system. It is important to note at this point that interfering substances of the type discussed herein affect only the indicator means and not the selected specific gravity-affected reaction, and as such can be eliminated by properly coordinating the indicator means and the type of liquid to be tested. However, interference of the selected reaction caused by the presence of solute in the test liquid is indispensable to the present invention.

It will be apparent from the foregoing that the present invention provides a new means for determining specific gravity which by virtue of its uncomplicated nature fulfills a long-felt need, particularly in the field of clinical medicine.

The present invention will now be illustrated, but is not intended to be limited, by the following examples.

EXAMPLE 1

In this example a composition and device of the present invention was prepared and used in testing urine samples having different specific gravities.

a. Preparation of test devices

An aqueous solution having the following proportions of ingredients was prepared as follows:

| | | |
|---|---|---|
| galactose oxidase | 13,091 | Worthington units[1] |
| peroxidase (2500 units/mg.) | 16.4 | mg. |
| bovine albumin | 1.09 | g. |
| o-tolidine . 2HCl | 0.108 | g. |
| sodium phosphate, monobasic | 0.181 | g. |
| sodium phosphate, dibasic | 0.552 | g. |
| Elvanol 51-05[2] | 1.09 | g. |
| 75% Aerosol OT[3] | 0.07 | g. |

|  |  |
|---|---|
| water | 59.4 ml. |

[1] Worthington Biochemical Corp., Freehold, New Jersey
[2] thickening agent from E.I. duPont de Nemours & Co., Wilmington, Delaware
[3] wetting agent from American Cyanamide Co., Wayne, New Jersey A sheet of SA2 ion exchange paper from Whatman, Inc., Cliffton, N.J. was immersed in the resultant solution and dried at 90° C. for about 10 minutes. Approximately 5 mm. square carrier sections or pads of the dry reagent-impregnated sheet were then attached to the surface of one end of 5 mm. by 85 mm. plastic strips using double-faced adhesive tape, thereby providing test devices as shown in FIG. 1.

b. Test method

The reagent pad portions of the test devices so made yielded a green color when momentarily immersed in an aqueous solution containing galactose. The color of an unreacted pad after rehydration by immersion in distilled water was cream. A color chart was constructed consisting of four different colors to which were assigned values of 0, 4, 8, and 12 respectively. The color having a value of 0 was that of a rehydrated, unreacted test strip pad. Green shades were assigned values 4, 8, and 12 with the deeper shades having the higher values.

Figure 5:
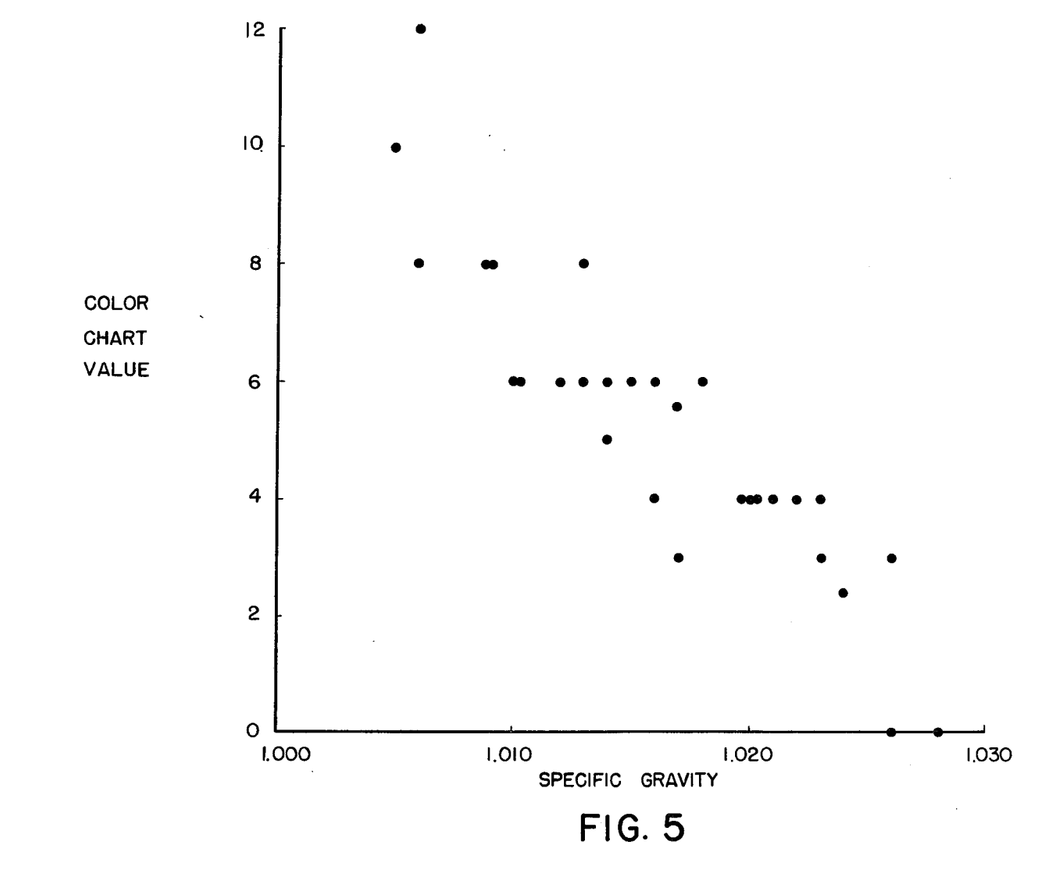
FIG. 5 is a graphical representation of the relationship between the specific gravity of a liquid and the visually observed colorimetric response produced by a preferred test composition in accordance with the present invention.

Twenty-nine (29) random urine specimens having ascorbate levels below 5 mg./100 ml. were collected and their specific gravities measured using a TS meter (B-5996) available from American Optical Co., Buffalo, N.Y. To 10 ml. volumes of each of the specimens were added 0.7 ml. of a 10% w/v galactose solution. The reagent pad portions of twenty-nine (29) of the previously prepared test devices were each momentarily dipped into a separate one of the galactose-treated urine samples. The color response produced after one minute was assigned an integer value between 0 and 12 based on a comparison with the color chart. The results appear in graphical form in FIG. 5 of the drawing.

It was thus demonstrated that the present invention provides a convenient, useful method for distinguishing high (>1.020), medium (1.010–1.020), and low (<1.010) levels of specific gravity in urine.

EXAMPLE 2

Figure 6:
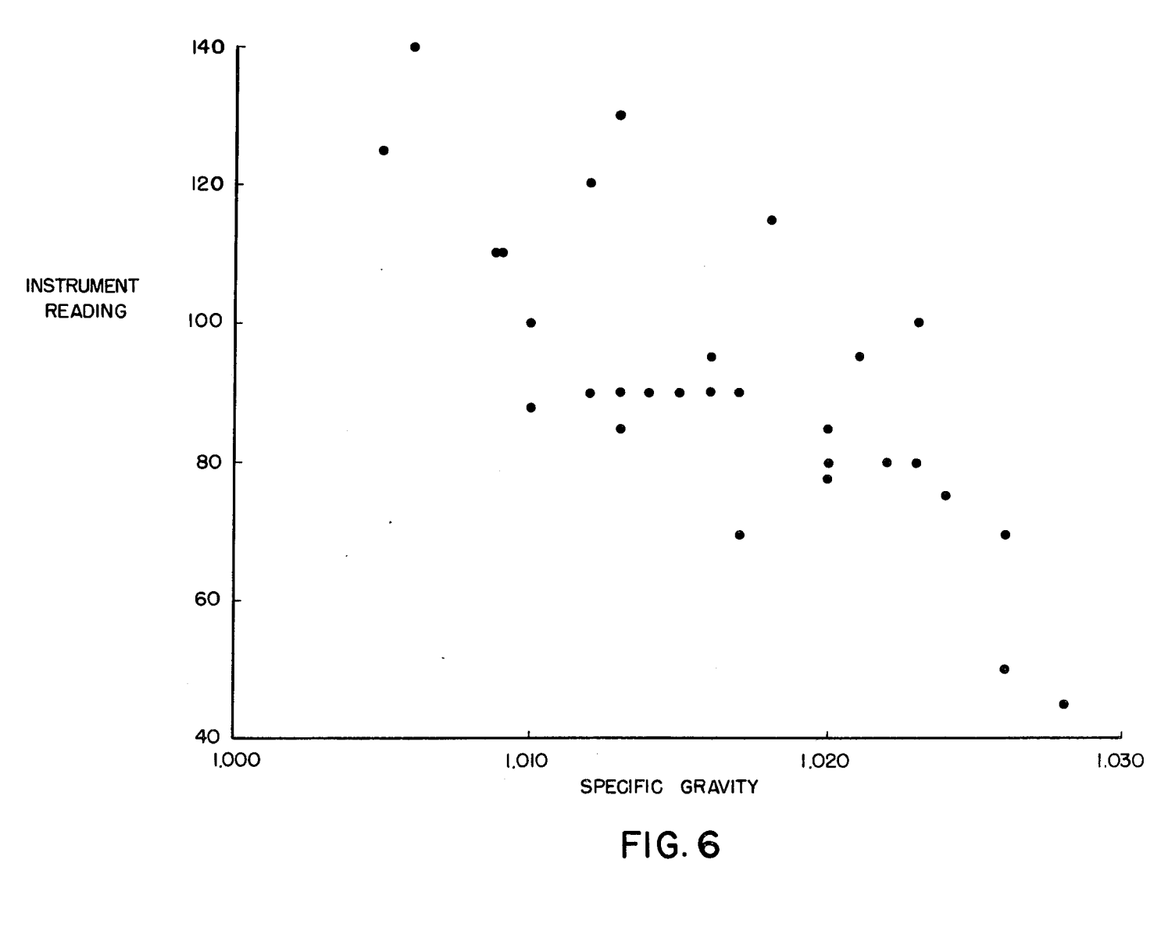
FIG. 6 is a graphical respresentation of the relationship between the specific gravity of a liquid and the instrumentally measured colorimetric response produced by a preferred test composition in accordance with the present invention.

Example 1 was repeated except that after 45 seconds from the time of contact between each urine sample and the respective test device pad the color response produced was measured in an Eyetone ® reflectance meter available from Ames Company Division of Miles Laboratories, Inc., Elkhart, Indiana. This instrument has maximum activity at 580 nm. The results appear in graphical form in FIG. 6 of the drawing.

It was thus demonstrated that the rate of color response produced by the standarized enzymatic galactose oxidation reaction is functionally related to the specific gravity of the test liquid.

EXAMPLE 3

In this example the effect of three major contributors to urinary specific gravity on a standardized chemical reaction was assessed.

Test devices were prepared as in procedure a. of Example 1. Four (4) sodium biphosphate, four (4) sodium chloride, and six (6) urea aqueous solutions having various specific gravities were prepared. To 10 ml. volume samples of the prepared solutions were added 0.1 ml. of a 10% w/v galactose solution. A separate one of the reagent pad portions of the previously prepared test devices was momentarily dipped into each of the galactose-treated solutions. The sample-inoculated pads were placed in an Eyetone ® reflectance meter, and the time (in seconds) required for the color reaction to reach a reading of 100 units was recorded. The results appear in tabular form below and in graphical form in FIG. 7 of the drawing.

Figure 7:
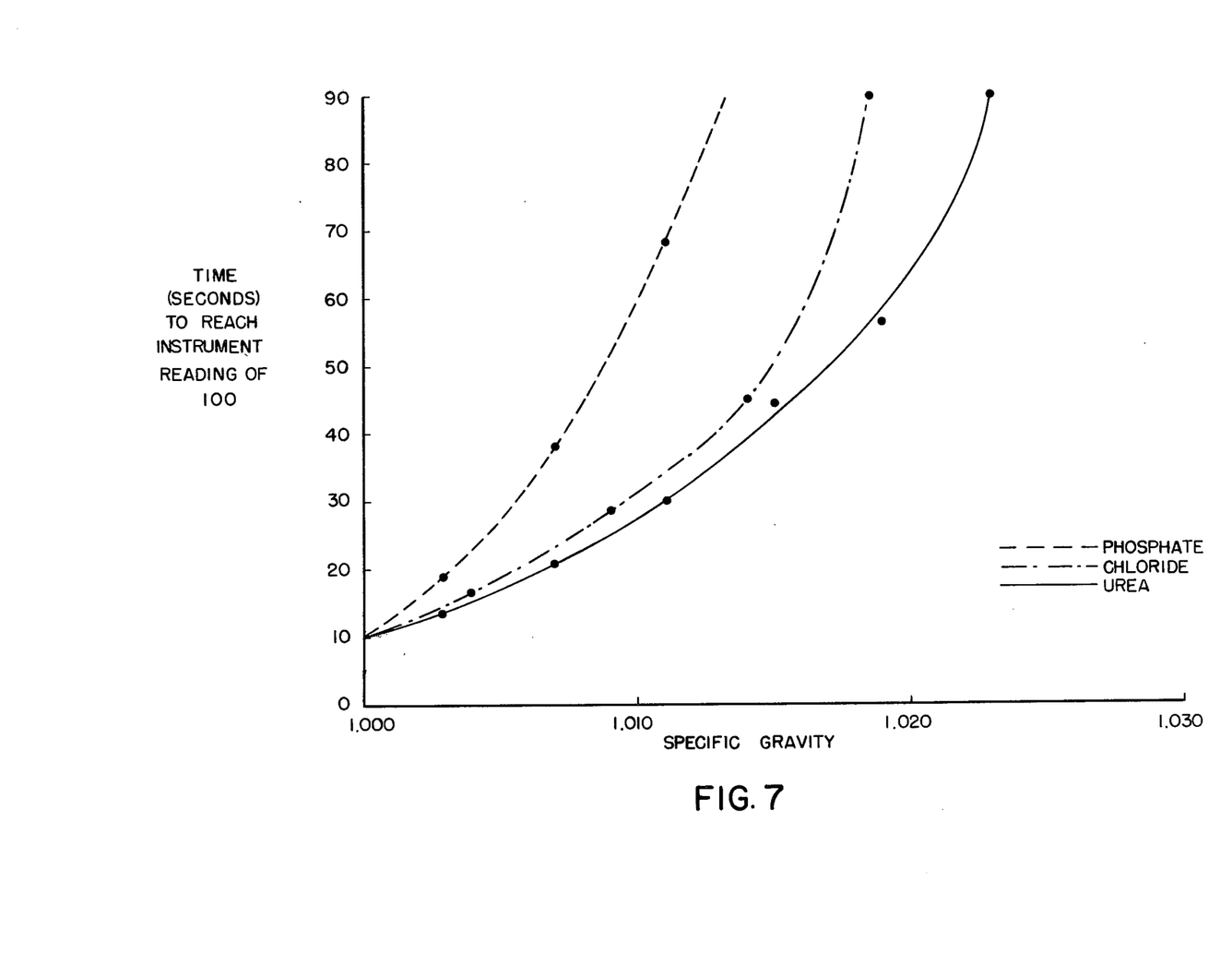
FIG. 7 is a graphical respresentation of the inhibition of a preferred standardized chemical reaction of the present invention caused by major constituents contributing to the specific gravity of urine.

| specific gravity contributor | grams added to 100 ml. water | specific gravity (T.S. meter) | time (seconds) to reach 100 reading | |
|---|---|---|---|---|
| phosphate ($NaH_2PO_4$) | 1 | 1.003 | 19 | 19 |
|  | 2 | 1.007 | 38 | 39 |
|  | 3 | 1.011 | 76 | 80 |
|  | 4 | 1.015 | 150 | 143 |
| chloride (NaCl) | 1 | 1.004 | 17 | 16 |
|  | 2 | 1.009 | 28 | 29 |
|  | 3 | 1.014 | 45 | 45 |
|  | 4 | 1.018 | 85 | 95 |
| urea | 1 | 1.003 | 13 | 14 |
|  | 2 | 1.007 | 21 | 21 |
|  | 3 | 1.011 | 30 | 30 |
|  | 4 | 1.015 | 44 | 45 |
|  | 5 | 1.019 | 58 | 55 |
|  | 6 | 1.023 | 95 | 85 |

It was thus demonstrated that major contributors to urinary specific gravity affect the standardized chemical reaction in a very similar manner, the effects produced by the two predominant contributors, chloride ion and urea, being essentially the same.

EXAMPLE 4

In this example test devices as in FIG. 1 were prepared and used in testing liquid samples having different specific gravities.

The test devices were prepared as in procedure a. of Example 1 except that the dry reagent-impregnated sheet of ion exchange paper was immersed in a 0.5% w/v solution of galactose in pyridine and air dried for about 10 minutes, after which it was cut into squares which were attached to plastic strips. The resultant test devices yielded color responses related to specific gravity upon contact with aqueous test samples which did not contain galactose. The test samples comprised two containing aqueous solutions of sodium biphosphate at 3% and 6% w/w concentrations respectively, two containing sodium chloride at 3% and 6% w/w concentrations respectively, and two containing urea at 3% and 6% w/w concentrations respectively. When contacted with the reagent pad portions of test devices as prepared in this example, each of the phosphate, chloride, and urea solutions produced a color response in the reagent pad portion contacted therewith. It was observed that in each case the 3% w/w solution produced a color response more rapidly than the 6% w/w solution.

EXAMPLE 5

In this example test devices as in FIG. 3 were prepared and used in testing the specific gravity of urine having a high ascorbate level.

Reagent-impregnated pads about 5 mm. square were prepared as in procedure a. of Example 1 and attached to plastic base members as the pad 32 in FIG. 3. Strips of E&D 204 paper available from Eaton-Dikeman Co., Mount Holly Springs, Pa. were immersed in an aqueous solution containing 500 mg./100 ml. galactose and allowed to dry. The dry galactose-impregnated strips were cut into approximately 5 mm. by 20 mm. pads and attached to the aforementioned base members as the pad 33 shown in FIG. 3.

These test devices were used in testing the specific gravity of urines having ascorbate levels above 5 mg./100 ml. and specific gravities of 1.006, 1.012 and 1.022 respectively. In testing the urine, the outer end portion of the pad 33 of each test device was dipped into the urine. After a short time, the sample flowed through the pad 33 and into the pad 32 of the test device whereupon a color response was produced in the pad 32. One minute after contacting a urine sample having a specific gravity of 1.022 the reagent pad portion 32 yielded a greenish color, whereas a dark blue-green color was produced in pad 32 when testing a urine sample having a specific gravity of 1.012.

One minute after contacting the pad 33 of a test device with a urine sample treated with galactose as in Example 1, having a specific gravity of 1.006 and containing 15 mg./100 ml. of ascorbate, the reagent pad portion 32 yielded a blue-green color. When the same urine sample treated with galactose was contacted by the pad 12 of the test device prepared as in Example 1, no color response was produced because of ascorbate interference.

It was thus demonstrated that the form of the invention shown in FIG. 3 permits the determination of specific gravity without interference from high ascorbate levels in urine samples tested therewith.

EXAMPLE 6

In this example test devices as in FIG. 4 were prepared and used in testing the specific gravity of urine.

A dry reagent-impregnated sheet of SA2 ion exchange paper was prepared according to the procedure a. of Example 1. Strips of E&D 204 paper were immersed in an aqueous solution containing 500 mg/100 ml. galactose and allowed to dry. Both the reagent-impregnated sheet and the galactose-impregnated strips were cut into approximately 5 mm. by 5 mm. sections or pads. Test devices were prepared by placing one pad of each type in a laminate fashion onto the surface of one end of a 5 mm. by 85 mm. plastic base strip. The laminate structure of FIG. 4 was produced by overlaying the superimposed pads with a piece of transparent plastic adhesive tape which was pressed onto the base strip as shown in FIG. 4.

When the laminated pad structure of test devices thus prepared were momentarily dipped into urine samples having a specific gravity of 1.020, a green color response was observed in the laminated pads whereas a dark blue-green color was produced in said pads were urine samples having a specific gravity of 1.005 were tested therewith.

EXAMPLE 7

In this example test devices as in FIG. 1 were prepared and used in testing urine samples having different specific gravities, the selected standardized chemical reaction involved being the enzymatic oxidation of glucose.

Test devices comprising reagent pad portions 12 as in FIG. 1 were impregnated with glucose oxidase, peroxidase, and a chromogen substantially as described in U.S. Pat. No. 3,453,180. Four (4) test solutions were prepared as follows. The first test solution was water containing 0.1% w/v glucose. The other three test solutions were urine samples which has specific gravities of 1.003, 1.011, and 1.027 respectively and which were adjusted to contain 0.1% w/v glucose. The reagent pad portions of four (4) of the test devices were each momentarily dipped into a separate one of the prepared test solutions. The color responses produced after 10 seconds were as follows:

| specific gravity of test solution | color response |
|---|---|
| 1.000 | deep purple |
| 1.003 | deep purple |
| 1.011 | purple |
| 1.027 | pale reddish-purple |

It was thus demonstrated that various specific gravity levels in an aqueous liquid can be distinguished using test devices in accordance with the present invention in which the selected standarized reaction involves the enzymatic oxidation of glucose.

EXAMPLE 8

In this example test devices as in FIG. 1 were prepared and used in testing urine samples having different specific gravities, the selected standardized chemical reaction involved being non-enzymatic, color-forming reaction sensitive to nitrite.

Solutions a. and b. were prepared as follows:

| Solution a. | | |
|---|---|---|
| p-arsanilic acid | 0.13 | g. |
| Gantrez AN[1] | 0.5 | g. |
| sodium lauroyl sarcosinate | 0.25 | g. |
| methanol | 75 | ml. |
| water | 25 | ml. |

[1]an equimolar copolymer of methylvinyl ether and maleic anhydride available from General Aniline and Film Corp., New York, New York

| Solution b. | | |
|---|---|---|
| N-(1-naphthyl)ethylene-diamine . 2HCl | 0.1 | g. |
| d-tartaric acid | 1.0 | g. |
| polyvinylpyrrolidone | 6.2 | ml. |
| Renex 698[2] | 0.1 | g. |
| chloroform | 75 | ml. |
| methanol | 18.8 | ml. |

[2]an ethoxylated nonyl phenol-wetting agent available from Atlas Chemical Industries, Wilmington, Delaware A sheet of Whatman No. 17 filter paper from W. R. Balston, Ltd, Maidstone, Kent, England, was immersed in Solution a. and dried at 110° C. for about 10 minutes. The filter paper sheet was then immersed in Solution b. and dried at 75° C. for about 10 minutes. Approximately 5 mm. square sections or pads of the dry reagent-impregnated sheet were attached to the surface of one end of 5 mm. by 85 mm. plastic strips using double-faced adhesive tape, thereby providing test devices as shown in FIG. 1.

Three (3) urine samples were obtained which had different specific gravities and ascorbate levels below 5 mg./100 ml. and which produced no observable color change upon contact with the reagent pads of the test devices thus prepared. Sodium nitrite was then added to each of the urine samples to a concentration of 0.5 mg/100 ml. The reagent pad portions of three (3) of the thus prepared test devices were each momentarily dipped into a separate one of the nitrite-treated samples. The color responses produced after one minute were as follows:

| specific gravity of test solution | color response |
|---|---|
| 1.005 | pink |
| 1.014 | pale pink |
| 1.026 | buff |

It was thus demonstrated that various specific gravity levels in an aqueous solution can be distinguished using test devices in accordance with the present invention in which the selected standardized reaction is non-enzymatic.

EXAMPLE 9

In this example test compositions were used in testing urine samples having different specific gravities, the selected standardized chemical reaction involved being a non-enzymatic, color-forming reaction sensitive to reducing sugars.

Test tablets comprising cupric sulfate, sodium hydroxide, and an effervescent couple were prepared substantially as described in U.S. Pat. No. 2,387,244. Three (3) urine samples having different specific gravities were obtained and the reducing sugar content of each was adjusted to a concentration of 0.35 g./100 ml. Five (5) drops of each sample were placed in a separate test tube. Ten (10) drops of water and one tablet thus prepared were added to each test tube. The following color responses were observed 15 seconds after the foaming caused by the effervescent couple had ceased:

| specific gravity of test solution | color response |
|---|---|
| 1.003 | yellowish-green |
| 1.011 | pea green |
| 1.027 | green |

It was thus demonstrated that various specific gravity levels in an aqueous solution can be distinguished using test compositions in accordance with the present invention in which the selected standardized reaction is non-enzymatic.

What is claimed is:

1. A method for determining the specific gravity of a urine sample, which method comprises the steps of:
   (a) contacting said sample with a predetermined concentration of an enzyme and of a reagent upon which said enzyme exerts its catalytic activity, the rate of reaction of said reagent in the presence of said enzyme being affected by the aggregate solute content of said sample,
   (b) determining the rate of said reaction in contact with said sample, and
   (c) comparing such determined reaction rate to the rates of said reaction when carried out in contact respectively with samples of urine having known different specific gravities.

2. A method as in claim 1 wherein the rate of said reaction is determined by measuring the rate of formation of a product of said reaction.

3. A method as in claim 2 wherein the rate of formation of said reaction product is measured by contacting said sample with indicator means responsive to the presence of said product and determining the rate of indicator response.

4. A method as in claim 2 wherein the response of said indicator means is colorimetric.

5. A method as in claim 4 wherein step (c) is accomplished by comparing with a standard color chart the color response of said indicator means at a predetermined time interval after contact of said sample with said indicator means.

6. A method as in claim 1 wherein said enzyme is an oxidoreductase.

7. A method as in claim 6 wherein said reaction involves the enzymatic oxidation of a carbohydrate to produce hydrogen peroxide.

8. A method as in claim 7 wherein said reagent is a hexose.

9. A method as in claim 7 wherein said enzyme is galactose oxidase and said reagent is galactose.

10. A method as in claim 7 wherein said enzyme is glucose oxidase and said reagent is glucose.

11. A test composition for determining the specific gravity of a urine sample, which composition comprises (1) a predetermined quantity of an enzyme and of a reagent upon which said enzyme exerts its catalytic effect, the rate of reaction of said reagent in the presence of said enzyme being affected by the aggregate solute content of said sample, and (2) indicator means responsive to the presence of a product of said reaction.

12. A composition as in claim 11 wherein the response of said indicator means is colorimetric.

13. A composition as in claim 11 which is in a dry form.

14. A test device for determining the specific gravity of a urine sample, which comprises the test composition of claim 11 and a carrier incorporated therewith.

15. A test device as in claim 14 wherein said carrier is absorbent relative to said sample.

16. A test device as in claim 14 which additionally comprises a base to which said carrier is attached.

17. A test device as in claim 14 which is prepared by impregnating said carrier with a first solution containing one of said enzyme and said reagent of said test composition, drying said carrier, impregnating said carrier with at least one other solution which contains the other of said enzyme and reagent and in which said reaction is incapable of occurring to a significant degree, and drying said carrier.

18. A test device as in claim 14 wherein the components of said test composition are dispersed in a material which is soluble in said sample.

19. A composition as in claim 11 wherein said enzyme is an oxidoreductase.

20. A composition as in claim 19 wherein said reaction involves the enzymatic oxidation of a carbohydrate to produce hydrogen peroxide.

21. A composition as in claim 20 wherein said indicator means is responsive to the presence of hydrogen peroxide and includes a substance having peroxidative activity and a chromogen which is oxidized in the presence of hydrogen peroxide and said substance having peroxidative activity to yield a colorimetric response.

22. A method as in claim 20 wherein said reagent is a hexose.

23. A method as in claim 20 wherein said enzyme is galactose oxidase and said reagent is galactose.

24. A method as in claim 20 wherein said enzyme is glucose oxidase and said reagent is glucose.

25. A test device for determining the specific gravity of a urine sample, which comprises a base, at least two carriers supported by said base, one of said enzyme and said reagent of the test composition of claim 11 being incorporated with at least one of said carriers, and the other of said enzyme and reagent being incorporated with at least one other of said at least two carriers.

26. A test device as in claim 25 wherein said carriers are attached to said base in laminate relation.

27. A test device as in claim 25 wherein at least one of said at least two carriers is incorporated with indicator means responsive to the presence of a product of said reaction.

28. A test device as in claim 27 wherein the response of said indicator means is colorimetric.

29. A test device as in claim 25 wherein said carriers are attached to said base.

30. A test device as in claim 29 wherein said carriers are spaced apart and movable into contact with one another.

31. A test device as in claim 29 wherein said carriers are in physical contact with each other.

* * * * *